United States Patent
Flores (10) Patent No.: US 10,668,195 B2
(45) Date of Patent: Jun. 2, 2020

(54) CATHETER PUMP WITH FIXED-DIAMETER IMPELLER

(71) Applicant: FBR Medical, Inc., Westport, CT (US)

(72) Inventor: Jesus Flores, Mission Viejo, CA (US)

(73) Assignee: FBR Medical, Inc., Westport, CT (US)

( * ) Notice: Subject to any disclaimer, the term of this patent is extended or adjusted under 35 U.S.C. 154(b) by 0 days.

(21) Appl. No.: 16/429,352

(22) Filed: Jun. 3, 2019

(65) Prior Publication Data
US 2019/0365973 A1 Dec. 5, 2019

Related U.S. Application Data

(60) Provisional application No. 62/679,312, filed on Jun. 1, 2018.

(51) Int. Cl.
*A61M 1/10* (2006.01)
*A61M 1/12* (2006.01)

(52) U.S. Cl.
CPC ........ *A61M 1/1024* (2014.02); *A61M 1/1008* (2014.02); *A61M 1/1013* (2014.02); *A61M 1/1031* (2014.02); *A61M 1/1034* (2014.02); *A61M 1/1086* (2013.01); *A61M 1/122* (2014.02); *A61M 2205/0222* (2013.01)

(58) Field of Classification Search
CPC .............. A61M 1/1024; A61M 1/1008; A61M 1/1013; A61M 1/1031; A61M 1/1034; A61M 1/122; A61M 1/1086; A61M 2205/0222
See application file for complete search history.

(56) References Cited

U.S. PATENT DOCUMENTS

| | | | |
|---|---|---|---|
| 6,245,007 B1 | 6/2001 | Bedingham et al. |
| 6,981,942 B2 | 1/2006 | Khaw et al. |
| 7,027,875 B2 | 4/2006 | Siess et al. |
| 7,241,257 B1 | 7/2007 | Ainsworth et al. |
| 8,298,169 B2 | 10/2012 | Yacoubian et al. |
| 8,485,961 B2 | 7/2013 | Campbell et al. |
| 8,579,858 B2 | 11/2013 | Reitan et al. |

(Continued)

FOREIGN PATENT DOCUMENTS

| | | | |
|---|---|---|---|
| WO | 98/53864 A1 | 12/1998 |
| WO | 00/43053 A1 | 7/2000 |

(Continued)

OTHER PUBLICATIONS

US 9,427,507 B2, 08/2016, Siess (withdrawn)
(Continued)

*Primary Examiner* — Catherine M Voorhees
*Assistant Examiner* — Roland Dinga
(74) *Attorney, Agent, or Firm* — Kaplan Breyer Schwarz, LLP (57) ABSTRACT

A catheter blood pump includes a catheter, an expandable impeller housing, a drive cable, and a fixed-diameter impeller. The drive cable, which is operatively coupled to an extracorporeal motor, conveys torque that drives rotation of the impeller. The catheter and impeller housing are movable independently of one another to alter the relative axial positions of the catheter, impeller housing, and the fixed-diameter impeller. This arrangement maximizes the diameter of the catheter blood pump's fixed-diameter impeller.

21 Claims, 7 Drawing Sheets

(56) References Cited

U.S. PATENT DOCUMENTS

| | | |
|---|---|---|
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,721,517 B2 | 5/2014 | Zeng et al. |
| 8,849,398 B2 | 9/2014 | Evans |
| 8,926,492 B2 | 1/2015 | Scheckel |
| 9,089,634 B2 | 7/2015 | Schumacher et al. |
| 9,446,179 B2 | 9/2016 | Keenan et al. |
| 9,717,833 B2 | 8/2017 | McBride et al. |
| 9,833,550 B2 | 12/2017 | Siess |
| 9,895,475 B2 | 2/2018 | Toellner et al. |
| 9,962,475 B2 | 5/2018 | Campbell et al. |
| 2006/0155158 A1 | 7/2006 | Aboul-Hosn |
| 2012/0059460 A1 | 3/2012 | Reitan |
| 2012/0178986 A1* | 7/2012 | Campbell ............ A61M 1/101 600/16 |
| 2014/0275726 A1 | 9/2014 | Zeng |
| 2015/0290372 A1 | 10/2015 | Muller et al. |
| 2015/0306291 A1 | 10/2015 | Bonde et al. |
| 2017/0072120 A1 | 3/2017 | Tanner et al. |
| 2018/0055979 A1 | 3/2018 | Corbett et al. |
| 2018/0169312 A1 | 6/2018 | Barry |

FOREIGN PATENT DOCUMENTS

| | | |
|---|---|---|
| WO | 2003/103745 A2 | 12/2003 |
| WO | 2017/162618 A1 | 9/2017 |

OTHER PUBLICATIONS

Authorized Officer Voula Tsogka, International Search Report and Written Opinion dated Oct. 7, 2019 issued in International PCT Application No. PCT/IB2019/054590.

G. Pesarini et al., "Impella-protected PCI: the clinical results achieved so far", "Minerva Cardioangiol.", Apr. 11, 2018, DOI: 10.23736/S0026-4725.18.04678-9, https://www.ncbi.nlm.nih.gov/pubmed/29642690.

M. Capoccia, 'Mechanical Circulatory Support for Advanced Heart Failure: Are We about to Witness a New "Gold Standard"?', "Journal of Cardiovascular Development and Disease", Dec. 12, 2016, DOI: 10.3390/jcdd3040035, 3(4), https://www.ncbi.nlm.nih.gov/pubmed/29367578.

V. Mendes et al., "Two Years of Experience in the Implantation of Heartmate III.", "Rev Port Cir Cardiotorac Vasc", Jul. 1, 2017, https://www.ncbi.nlm.nih.gov/pubmed/29701352.

* cited by examiner

CATHETER PUMP WITH FIXED-DIAMETER IMPELLER

Statement of Related Cases

This case claims priority to U.S. Pat. App. 62/679,312 filed Jun. 1, 2018 and which is incorporated by reference herein.

FIELD OF THE INVENTION

This invention relates generally to catheter pumps.

BACKGROUND OF THE INVENTION

Some patients who have heart failure, and some of those at risk for developing it, receive interventions intended to temporarily assist the heart before or during a medical or surgical procedure and/or during a recovery period. The intervention typically lasts for less than a week, but can continue for several weeks. These interventions include pharmaceuticals and/or medical devices, including cardiac-assist devices.

Some cardiac-assist devices include a pump to supplement the heart's pumping action. By assuming some of the heart's pumping function, these "blood pumps" unload the heart, helping it to recover. Cardiac-assist devices can be temporary or permanent.

Some blood pumps have an extracorporeal (i.e., outside the body) impeller to drive blood flow. Some of these extracorporeal blood pumps connect to a patient's heart and blood vessels directly through the exposed chest using relatively large-diameter tubes (cannulas). Such procedures, performed by cardiac surgeons, are invasive and may require cardiopulmonary bypass. They are, unfortunately, associated with significant complications. Some other extracorporeal blood pumps connect to the patient using relatively wide catheters or cannulas, inserted through peripheral blood vessels.

Some other blood pumps are percutaneous, wherein the impeller (and in some devices, the pump's motor) temporarily reside within the patient. These blood pumps are often coupled to a catheter, and are consequently referred to as "catheter blood pumps." Some catheter blood pumps are inserted into the patient using established cath-lab techniques, wherein they are advanced through the vascular system (typically the femoral artery) to a patient's heart. This approach is significantly less invasive than cardiac surgery or other relatively complicated procedures.

It is desirable for a catheter blood pump to have as small a diameter as possible, preferably less than 16 Fr, and more preferably less than 12 Fr, to minimize trauma to the vasculature or trauma associated with the surgery performed for insertion. It is also desirable for such a pump to have a large pumping capacity, preferably 2 liters per minute or even more, to provide sufficient circulation for a patient. Additionally, such a pump must avoid, to the extent possible, damaging the blood in the form of hemolysis (i.e., destruction of red blood cells).

Indeed, notwithstanding its attractiveness as a less-invasive alternative, most designs for percutaneously-inserted blood pumps exhibit one of more of the following shortcomings:
 a limited pump flow;
 some degree of hemolysis;
 require the use of a large catheter/cannular, with a risk of ischemia; and
 they are expensive.

There have been previous attempts, mostly unsuccessful, to increase the flow rate through catheter blood pumps. Simply increasing the rotation speed of the pump's impeller will increase the flow rate. However, the increased speed results in additional power requirements, which in turn may increase the size and electrical demands of the motor. In devices that use a flexible drive cable to drive the pump's impeller (rather than an in-vivo motor sited near the impeller), the increased motor speed may require an increase in the size and stiffness of the flexible drive cable. Furthermore, the increased speed of the impeller causes increased shear stress on the blood, resulting in increased hemolysis. Also, greater motor speeds increase the likelihood of drive-cable failure.

As mentioned above, catheter blood pumps are usually advanced to the heart through the vascular system. Consequently, there is a limit as to the acceptable diameter of the largest feature of the catheter blood pump. Consider that such a blood pump typically includes various tubes, an impeller housing, an impeller, and a drive cable. Since the impeller is rotating at high speed (thousands of rpm), it is important that the impeller does not come into contact with the patient's anatomy or other parts of the blood pump (e.g., tubing, impeller housing, etc.). For a pump having a fixed-diameter, non-foldable/non-expandable impeller, an outer-most tube, typically called a sheath is typically the largest-diameter feature, whereas other elements of the blood pump (e.g., impeller housing, impeller, etc.) that are intended to be introduced into the vasculature are contained within the sheath. As a consequence, the diameter of the impeller is necessarily smaller than the sheath and smaller than the impeller housing. This typically results in an impeller having a diameter in the range of 9 to 12 Fr, which presents a significant limitation to generating pump flows greater than about 2 liters/minute.

In recognition of this problem, catheter blood pumps having an expandable impeller have been proposed. An expandable impeller collapses to a very small diameter (e.g., by folding/bending/hinging the impeller blades, etc.) to fit within a tube (e.g., sheath, etc.) for insertion into the body, and delivery via the vasculature to the aorta or heart. Once the pump is positioned, the expandable impeller is freed from the confines of the tubing (e.g., such as by partially retracting the tubing, etc.) and then expands to a larger diameter that could not otherwise be accommodated by the patient's vasculature. Usually, the expandable impeller is accompanied by an expandable impeller housing that is freed from the sheath/tubing at the same time as the expandable impeller, enabling both to expand in diameter.

This larger-diameter impeller develops, at least theoretically, a notably greater pumping capacity than would otherwise possible. However, expandable-impeller designs present significant implementation challenges, including the design of the impeller itself, as well as issues related to repeatedly and accurately controlling the gap between the rapidly rotating impeller blades and the surrounding impeller housing. Furthermore, experimentation and simulation (i.e., computational fluid dynamics) have shown that most proposed expandable impeller designs are relatively inefficient for generating blood flow as compared to what is achievable with some fixed-diameter impeller designs.

SUMMARY OF THE INVENTION

Embodiments of the invention provide a catheter blood pump that avoids some of the costs and disadvantages of the prior art, including, for example and without limitation, a need to generate sufficient blood flow by running a pump's impeller at high speeds or by using an expandable impeller.

The inventor recognized that the limitation on the size of a fixed-diameter impeller of a catheter blood pump could, quite surprisingly, be partially relaxed by utilizing a hybrid approach that combines elements of an expandable catheter blood pump—namely an expandable impeller housing—with elements of a non-expandable catheter blood pump, such as a fixed-diameter impeller.

The salient elements of the present catheter blood pump include a sheath, an expandable impeller housing, and a fixed-diameter impeller. In the illustrative embodiment, a drive cable, which is operatively coupled to an extracorporeal motor, conveys torque that drives the rotation of the impeller.

In some embodiments, the sheath and the expandable impeller housing of the catheter blood pump are movable—axially displaceable—independently of one another. This enables the relative axial positions of the sheath, expandable impeller housing, and the fixed-diameter impeller to be alterable with respect to one another, allowing the catheter blood pump to attain different states or configurations. These different states facilitate various phases of use: insertion of the pump into the vasculature and advancement to the pumping site, pumping operations, and removal of the pump from the patient.

In the illustrative embodiment, the catheter blood pump is physically adapted to achieve two main configurations/states, including:

- a first configuration/state for insertion into a peripheral artery (e.g., femoral, etc.) and advancement towards the heart, or removal therefrom. In this first configuration, the expandable impeller housing, but not the fixed-diameter impeller, is situated within the sheath.
- A second configuration/state, which is an operational state, wherein the expandable impeller housing is free from the confines of the sheath, and the fixed-diameter impeller is sited within the proximal end of the expandable impeller housing.

In attaining the aforementioned configurations/states, the catheter blood pump may adopt certain intermediate states to transition between the first and second states referenced above.

In the illustrative embodiment, the respective axial locations of the sheath and expandable impeller housing are alterable by user interaction, which occurs near the proximal end of the catheter blood pump. This interaction is accomplished via an actuation system, which in the illustrative embodiment includes two slideable members that are disposed in an extracorporeal handle. One slideable member couples to the sheath and the other slideable member couples to expandable impeller housing. Sliding one of these members along the handle causes the sheath to retract or advance; sliding the other member causes the expandable impeller housing to retract or advance.

Embodiments of the invention provide a catheter blood pump wherein the diameter of the fixed-diameter impeller, rather than that of any structure that surrounds it (e.g., impeller housing, sheath, etc.), is the feature that bumps up against the limit imposed by the diameter of the vasculature. In such embodiments, the diameter of the fixed-diameter impeller is at least as large as the outer diameter of any other feature of the catheter blood pump that enters the body. Simply put, for a catheter blood pump having a fixed-diameter impeller, embodiments of the invention maximize the impeller's diameter.

Because the impeller used in embodiments in accordance with the present teaching has a fixed diameter and therefore does not expand, it can be designed based on hemodynamic and pumping-efficiency considerations, and without regard to the implementation details of an expandable impeller. This results in a more efficient impeller design. Additionally, as a consequence of its relatively large size (c.a., fixed-blade circle diameter in the range of about 14 Fr to about 16 Fr), as compared to other fixed-diameter impellers, the present fixed-diameter impeller can be rotated at a relatively lower rotational speed for generating a given amount of pump flow than fixed-diameter impellers used in existing catheter blood pumps. This decreased rotational speed results in reduced shear stress, and, hence, decreased hemolysis of the patient's blood.

In some embodiments, the catheter blood pump comprises:
a fixed-diameter impeller having a first diameter;
a sheath, wherein the sheath is the largest of the fixed diameter tubes, and wherein, as a consequence of the first diameter, the fixed-diameter impeller cannot fit within the sheath;
an impeller housing, wherein the impeller housing is expandable and contractible in diameter; and
an actuator, wherein the actuator is operable to cause to the impeller housing to expand in diameter to place the catheter blood pump in a first state, and to cause the impeller housing to contract in diameter to place the catheter blood pump in a second state, wherein:
a) in the first state, the catheter blood pump is configured for pumping operations, wherein (i) the impeller housing is in an expanded-diameter state, and (ii) the fixed-diameter impeller is disposed in the impeller housing; and
b) in the second state, the catheter blood pump is configured for movement through the vascular system, wherein (i) the impeller housing is in a contracted-diameter state and is disposed within the sheath, and (ii) the fixed-diameter impeller is not contained in any tube or other structure of the catheter blood pump.

In some other embodiments, the catheter blood pump comprises:
a fixed-diameter impeller having a first diameter;
a sheath having a second outer diameter, wherein the first diameter is at least as large as the second outer diameter;
an impeller housing having:
(a) a first state, wherein the impeller housing resides within the sheath and further wherein the fixed-diameter impeller does not reside in the impeller housing or the sheath and is at a distal end of the catheter blood pump, and
(b) a second state, wherein the impeller housing is external to the sheath and wherein the fixed-diameter impeller is within the impeller housing and at a proximal end thereof.

In some additional embodiments, the catheter blood pump comprises:
a fixed-diameter impeller having a first diameter;
a drive cable operatively coupled to a motor at a proximal end thereof, and operatively coupled to the fixed-diameter impeller at a distal end thereof;
a sheath, wherein the sheath has a second diameter, which is the outer diameter thereof and the largest diameter of any of the plurality of fixed-diameter tubes, and wherein the first diameter is at least as large as the second diameter; and
an impeller housing having:
(a) a collapsed state wherein the impeller housing resides with the sheath, and
(b) an expanded state wherein the impeller housing is external to the sheath and has an inner diameter greater than the first diameter.

In yet some other embodiments, the catheter blood pump comprises:

a fixed-diameter impeller, wherein the fixed-diameter motor is operatively coupled to a motor, the fixed-diameter impeller having a first diameter;

an impeller housing that is expandable from a collapsed state to an expanded state;

a sheath, wherein the sheath has the largest external diameter of the plurality of fixed-diameter tubes, and wherein the first diameter of the fixed-diameter impeller is too large for the fixed-diameter impeller to reside within the sheath; and an actuator, wherein the actuator is physically adapted to place the catheter blood pump in at least two physical configurations, including:

a) a first configuration in which the impeller housing within the sheath in the collapsed state, and in which the fixed-diameter impeller is distal relative to the impeller housing and is a distal-most feature of the catheter blood pump, and b) a second configuration in which the impeller housing is external to and substantially distal of the sheath and is in the expanded state, and wherein the fixed-diameter impeller is disposed within the impeller housing at a proximal end thereof.

BRIEF DESCRIPTION OF THE DRAWINGS

To facilitate readability, features are not necessarily drawn to scale due to the wide range in features sizes of the catheter blood pump. Furthermore, internal views are likely to show some, but not all features, in cross section, as appropriate for best conveying the features relevant to the accompanying description. For the same reason, not all internal features are represented by "dashed" lines, as is conventional.

DETAILED DESCRIPTION

Definitions. The following words are defined for use in conjunction with this specification, including the appended claims.

About or Substantially means +/−15% of a nominal figure.

Axial, when referring to the orientation of a device or feature, references a direction that is parallel to the orientation of the drive cable at the location at which the device/feature is present (along the drive cable).

Catheter or Catheter assembly, as these terms are used in the blood-pump art and herein, refer en masse to the plurality of tubes that form part of the catheter blood pump.

Distal and Proximal. In the context of the catheter blood pump described herein, "distal" means relatively further from a first end of a drive cable that connects a drive motor to an impeller. The drive motor is located at the proximal end of the drive cable and the impeller is disposed at the distal end of the drive cable. Reference to the "distal" end of a particular feature of the catheter blood pump (e.g., an impeller housing, a bearing, etc.) means the end that is relatively further advanced in the vasculature (or relatively closer to distal end of the drive cable). Conversely, reference to the "proximal" end of a particular feature of the catheter blood pump means the end that is relatively closer to the proximal end of the drive cable.

Fixed-diameter impeller. This terms refers to an impeller that, regardless of the configuration/state of the pump (i.e., whether configured for insertion, advancement through the vasculature, pumping, or removal from the vasculature), the blade circle delimited by the perimeter of the blades is constant when viewed axially. In other words, the blades are not in any way bent or folded to define a relatively smaller blade circle (such as for advancement through the vasculature), only to expand, unfurl, etc., to define a relatively large blade circle for pumping operations. Reference to the "diameter" of the fixed-diameter impeller refers to the diameter of the blade circle.

Operatively coupled means that the operation of one device affects another device. For example, if a drive cable is "operatively coupled" to an impeller, it is capable of driving the impeller (i.e., causing the impeller to rotate). Operatively coupled devices need not be directly physically coupled to one another (i.e., there can be intermediate linkages, such as other devices, tubes, fluids, etc., between operatively coupled devices.

Proximate means "near to."

Other definitions may be provided in context later in this disclosure.

The illustrative embodiment of present invention is a catheter blood pump. The catheter blood pump is a percutaneous device; a portion of it remains outside of a patient's body (extracorporeal) and a portion is inserted into the patient (in-vivo) and advanced to the heart or proximate thereto. In particular, and among other elements, the blood pump's fixed-diameter impeller and impeller housing are inserted into the patient. For convenience, the phrase "pump assembly" is used herein to refer to the fixed-diameter impeller, impeller housing, and other distal features of the catheter blood pump.

There are several potential placement locations for the pump assembly. Most preferred for the illustrative embodiment of the catheter blood pump is across the aortic valve. Other potential locations include the ascending aorta or within the left ventricle. Such locations will require additional features, such as a "snorkel" for crossing the aortic valve. The pump assembly can be sited in other less-preferred locations, such as, without limitation, in the descending aorta, in suitably-sized peripheral blood vessels, or even in the right side of the heart or in right-side-related vasculature. At such alternate locations, one or more modifications are required to the illustrative embodiment, which, in conjunction with the present disclosure, are within the capabilities of those skilled in the art. For example, if sited in the right-side-of-the-heart or in right-side-related vasculature, modifications would be required to the impeller design, impeller rotation direction, as well as other features.

Figure 6:
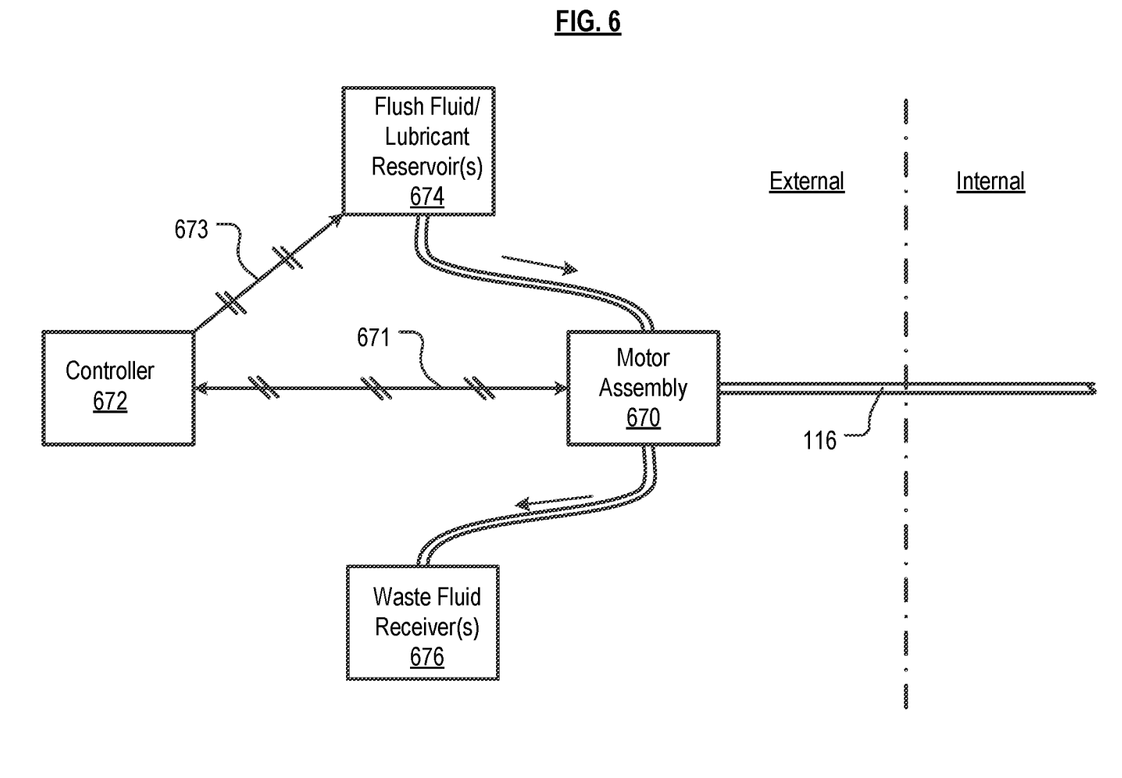
FIG. 6 depicts extracorporeal features of the catheter blood pump of FIG. 1A.

FIG. 6 depicts the extracorporeal elements of a catheter blood pump in accordance with an embodiment of the present invention, including motor assembly 670, controller 672, flush-fluid/lubricant reservoir(s) 674, and waste-fluid receiver(s) 676.

In some embodiments, motor assembly 670 includes a motor, an interface between drive cable 116 and the drive motor (e.g., fluid seals, etc.), fluidic connectors and a manifold for introducing fluids (for flushing, lubrication, etc.) to portions of the catheter blood pump (e.g., bearing surfaces, drive cable, etc.), power and signal connectors, sensor interfaces, and a housing to contain all such elements.

The motor of motor assembly 670 drives the pump assembly, and is capable of operating in a range of about 5,000 rpm to about 50,000 rpm. In some embodiments, the motor is a brushless DC servomotor with speed detection and regulation. The motor is suitable for driving the pump assembly to provide an average pump flow of 2.5 or more liters per minute at 60 mm Hg average pressure differential across the pump at a fluid viscosity of about 4 cP at 37° C. It will be understood that the specific power output requirement of the motor will be dependent on impeller design (i.e., pump efficiency) and the diameter of the delivery system, among other factors. Those skilled in the art will know how to specify a motor as a function of system design and performance requirements.

In some embodiments, such as disclosed later in this specification in conjunction with FIGS. 4A and 4B, motor assembly 670 is in the form of a handle, and, in addition to the aforementioned functionality, includes functionality for altering the configuration of the catheter blood pump.

Controller 672 is electrically connected to motor assembly 670 via signal line 671 and, in the illustrative embodiment, is also electrically connected to flush-fluid/lubricant reservoir(s) 674, such as by signal line 673. In the illustrative embodiment, controller 672 includes a power supply, motor-controller electronics, sensor electronics, and a display. Controller 672 typically provides one or more of the following functions, in addition to any others:
electrical drive (power) for the motor;
control signals for the motor;
controls the release of flush fluid/lubrication from reservoir(s);
receives and processes sensor data (e.g., blood pressure readings, etc.);
monitors system performance;
displays impeller speed and pump flow; and
provides auditory and/or visual alerts.

Flush-fluid/lubricant reservoir(s) 674 contains one (or more fluids) that are conveyed to motor assembly 670 and from it through tubing to bearing surfaces and the drive cable for flushing wear debris and/or providing lubrication. As previously noted, in some embodiments, controller 672 controls delivery of fluids from reservoir(s) 674. A variety of flush fluid and lubricants are suitable for use in conjunction with the catheter blood pump, including saline, glucose, or various commercially available solutions, as known to those skilled in the art, including, without limitation, a heparin/D5W solution. Waste lubricant and/or flushing fluid is conveyed back to motor assembly 670 from tubing and then expelled to waste fluid receiver(s) 676.

In the illustrative embodiment, drive cable 116, as well other tubing forming part of the catheter described later herein but not depicted in FIG. 6, is coupled to motor assembly 670. In various embodiments, some of such other tubing is fluidically coupled to flush-fluid/lubricant reservoir(s) 674 via a manifold or other fluid distribution arrangement within motor assembly 670. In the illustrative embodiment, drive cable 116 is operatively coupled to the motor to receive torque therefrom and transfer it, ultimately, to a fixed-diameter impeller disposed near the distal end of the catheter blood pump. Drive cable 116, the aforementioned tubing, as well as other distally located features of the catheter blood pump are inserted into and pass through a patient's vasculature in preparation for pumping operations. In some other embodiments, the motor is part of the in-vivo portion of the catheter blood pump such that a drive cable is not required. In such embodiments, the motor's drive shaft couples, more or less directly, to the impeller's drive shaft.

Figure 1A:
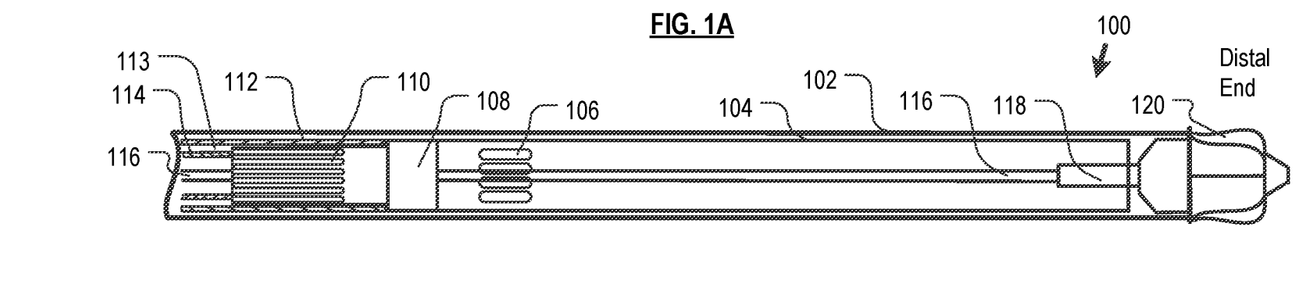
FIG. 1A depicts a distal portion of a catheter blood pump in accordance with the illustrative embodiment of the invention.

Referring now to FIG. 1A, the distal portion of catheter blood pump 100 in accordance with the present invention is depicted. The salient elements depicted in FIG. 1A include sheath 102, impeller housing 104, bearing 108, outer tube 112, inner tube 114, drive cable 116, and fixed-diameter impeller 120, configured as shown. As depicted in FIG. 1A, catheter blood pump 100 is in a configuration suitable for insertion into, and movement through, a patient's vascular system.

In the illustrative embodiment, sheath 102 extends, at its proximal end, from motor assembly 670 (see FIG. 6), to a distal end, such that its length is sufficient to reach the heart after insertion into a peripheral vessel. The required length of the sheath will vary as between children and adults, males and females, and as between large and small adults; typically, the length of the sheath, including a portion that remains extracorporeal, is in a range of about 1 to about 2 meters.

Sheath 102 has the largest diameter of any of the fixed-diameter tubes of catheter blood pump 100 that are inserted into the vasculature. The diameter of fixed-diameter impeller 120 is at least as great as the outer diameter of sheath 102. The sheath will typically have a diameter in the range of about 9 to about 16 Fr.

Figure 1B:
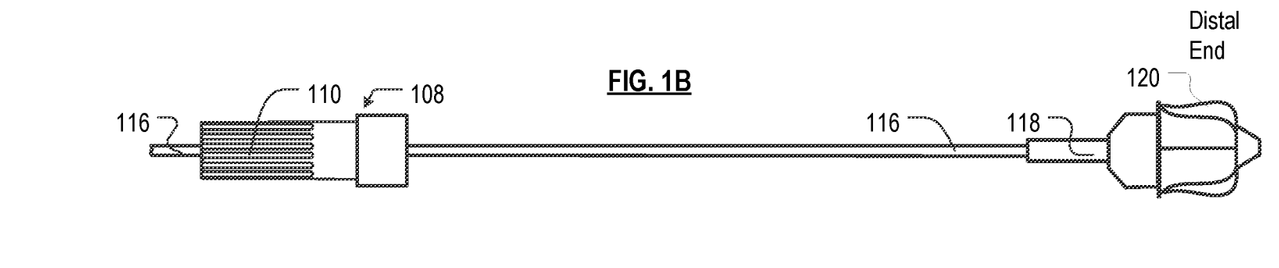
FIG. 1B depicts the distal portion of the catheter blood pump of FIG. 1A with certain features omitted for clarity.

With continuing reference to FIG. 1A, and referring also to FIG. 1B, drive cable 116 extends essentially the full length of catheter blood pump 100, from motor assembly 670 (see FIG. 6) to fixed-diameter impeller 120. Drive cable 116 transmits torque from the drive motor to fixed-diameter impeller 120, causing the impeller to rotate at high speeds. Drive cable 116 couples to the fixed-diameter impeller at impeller drive shaft 118. The drive cable must be flexible to advance fixed-diameter impeller 120 to its operational location in or proximate to the heart. In some embodiments, drive cable 116 comprises a multi-layer coil of wires, such as described in U.S. Pat. No. 9,962,475, incorporated by reference herein. The drive cable has a diameter in the range of about 0.05 to about 0.1 millimeters (mm) (about 0.002 to about 0.004 inches).

As configured for insertion into a patient, passage through the vascular system, and removal from the patient, fixed-diameter impeller 120 is the distal-most major feature of catheter blood pump 100. By virtue of its fixed diameter, wherein it does not expand, unfurl, unbend, etc., fixed-diameter impeller 120 can be designed so that its hemodynamic performance is optimized, as opposed to designing around constraints inherent in designing an expandable impeller.

In some embodiments, fixed-diameter impeller 120 comprises a soft, compliant material such as a polyether block amide. Using compliant material reduces the trauma caused to the vasculature during insertion. The durometer of material used to form the impeller is chosen to accommodate/compensate for impeller flex. One such material suitable for use is Pebax® brand therrmoplastic elastomers, commercially available from Arkema (King of Prussia, Pa.). Pebax® brand thermoplastics are available in a wide variety of grades, including those specifically approved for medical use. It is within the capabilities of those skilled in the art to select an appropriate medically-approved grade of Pebax® for use in conjunction with the present invention.

In some embodiments, fixed-diameter impeller 120 is reinforced via a ribbon made from a shape-memory alloy, such as Nitinol (nickel titanium). In some embodiments, the fixed-diameter impeller is designed to accept a guide wire, such as by creating a channel at its tip, to allow for rapid-exchange guide wire.

Impeller drive shaft 118, which extends from fixed-diameter impeller 120, couples to drive cable 116. Since drive cable 116 is flexible, drive shaft 118 is rigid to provide, along with bearing 108, stability to rotating fixed-diameter impeller 120 to keep it on center (within impeller housing 104). Drive shaft 118 comprises stainless steel tubing, such as hypo tube, or another rigid, medically-suitable material. In some embodiments, fixed-diameter impeller 120 is over molded onto a hypo tube.

Bearing (i.e., sleeve bearing) 108 accepts drive cable 116. The bearing is made from an abrasion-resistant material having lubricity properties, since its inner surface abuts drive cable 116, which, during operation, may be rotating at speeds in excess of 5,000 rpm. In some embodiments, bearing 108 comprises polyether ether ketone (PEEK), polyethylene terephthalate (PET), polytetrafluoroethylene (PTFE), or the like. In some embodiments, most of the inner surface of bearing 108 comprises low-friction surface 109 (see FIG. 1D), which expands the choice of materials for other portions of the bearing.

Figure 1C:
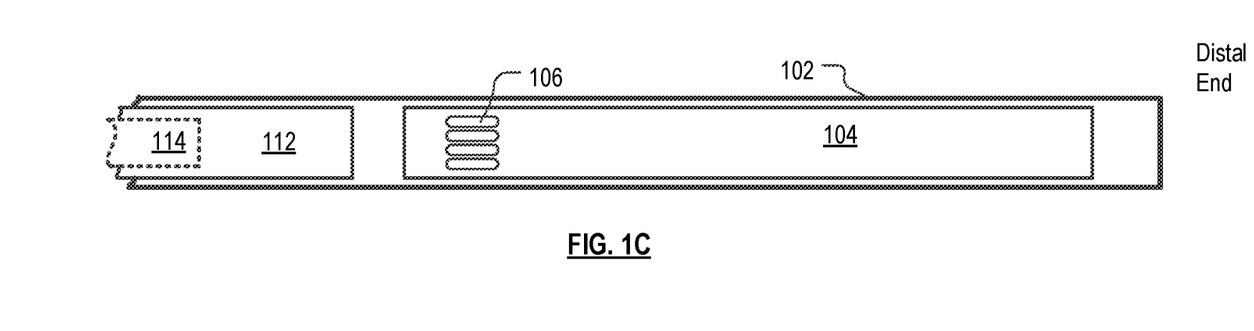
FIG. 1C depicts the features of the catheter blood pump of FIG. 1A that are omitted from FIG. 1B.

With continuing reference to FIGS. 1A and 1B, and referring now to FIG. 1C, impeller housing 104 is disposed within sheath 102 at a location distal to bearing 108. The proximal end of impeller housing 104 is attached to the distal end of bearing 108. Impeller housing 104 is expandable; it is constrained to a relatively smaller diameter while within sheath 102, and is free to expand to a relatively larger diameter when unconstrained by the sheath. The size of a gap between fixed diameter impeller 120 and the impeller housing 104, when expanded, is an important design consideration as it influences pump performance. Gap size can be determined, for example, via computational fluid dynamics, and is within the capabilities of those skilled in the art. This gap is typically in the range of about 0.025 to about 0.127 mm (about 0.001 to about 0.005 inches). The length (i.e., axial direction) of impeller housing 104 is typically in the range of 75 to about 102 mm (about 3 to about 4 inches).

In the illustrative embodiment, impeller housing 104 includes a plurality of openings 106 sited nearest its proximal end. As described later herein, openings 106 allow blood that is drawn in through the distal end of the impeller housing by action of fixed-diameter impeller 116 to flow out of the impeller housing. Based on its positioning within, for example, the left ventricle of the heart, this enables the pump to deliver blood across the aortic valve to the ascending aorta.

In some embodiments, impeller housing 104 is made from a Nitinol, laser-cut tubing, or braided Nitinol wire. In some embodiments, the impeller housing is covered with a thin membrane; for example, polyethylene terephthalate (PET) material braided into nitinol wire and then heat bonded together.

Figure 1D:
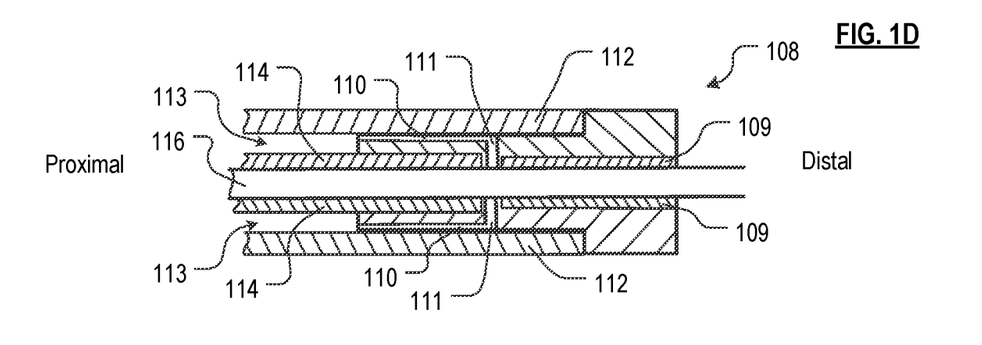
FIG. 1D depicts details of a bearing and associated features of the catheter blood pump of FIG. 1A.

Referring additionally to FIG. 1D, outer tube 112 and inner tube 114 couple to bearing 108 at their respective distal ends. In the illustrative embodiment, respective proximal ends of these tubes extend to motor assembly 670/handle 422 (see FIGS. 4A, 4B). In some embodiments, inner tube 114 comprises a medically suitable grade of PEBAX and in some embodiments is lined with PEEK or polytetrafluoroethylene (PTFE)-lined composite tubing. In some embodiments, inner tube 114 is made from multi-durometer tubing to enable bending at specified locations (as dictated by the anatomy). In some embodiments, outer tube 112 is not lined, but is likewise made of a medically suitable grade of PEBAX. Like inner tube 114, in some embodiments, outer tube 112 is made from multi-durometer tubing to enable bending at specified locations. Outer tube 112 has a diameter in the range of about 2.5 to about 3.6 mm (about 0.100 to about 0.140 inches) and inner tube 114 has a diameter in the range of about 1.5 to about 2.3 mm (about 0.06 to about 0.09 inches).

The inner and outer tubes are spaced apart by annular gap 113. The annular gap receives fresh flush fluid/lubricant delivered from flush fluid/lubricant reservoir(s) 674 (see FIG. 6). The external surface of the proximal portion of bearing 108 includes a plurality of surface grooves 110. These grooves receive the fresh flush fluid/lubricant flowing from annular gap 113. The distal end of at least two of surface grooves 110 includes through holes 111, which extend from the surface of associated grooves 110 to the inner surface of bearing 108 (adjacent to drive cable 116). The fresh flush fluid/lubricant flows through the holes and flows onto drive cable 116. The fresh flush fluid/lubricant is under pressure and flows to the proximal end of drive cable 116, carrying any debris generated from rotation of the drive cable, etc., back to motor assembly 670, at which location it is drained to waste fluid receiver(s) 676. The gap between drive cable 116 and inner tube 114 is in the range of about 0.05 to about 0.08 mm (about 0.002 to about 0.003 inches).

Figure 2A:
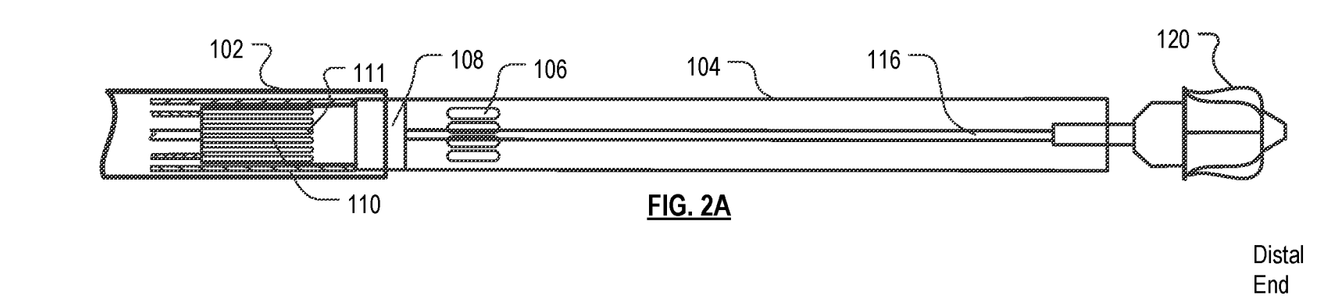
FIG. 2A depicts a first configuration of the distal portion of the catheter blood pump of FIG. 1A.
Figure 2B:
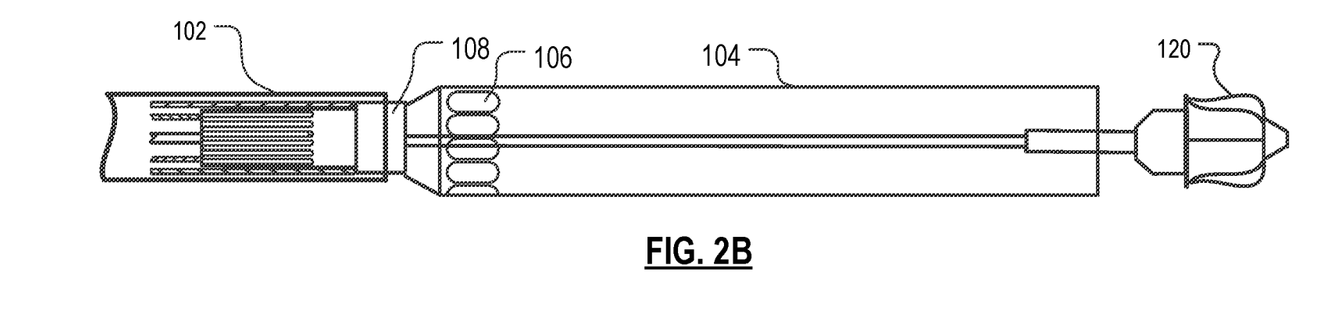
FIG. 2B depicts a transitional configuration of the distal portion of the catheter blood pump of FIG. 1A.

FIGS. 2A and 2B depict the distal end of catheter blood pump 100; FIG. 2A depicts impeller housing 104 in a compressed state whereas FIG. 2B depicts impeller housing 104 in an expanded state. In both of these figures, sheath 102 is partially retracted back to bearing 108, enabling impeller housing 104 to expand. In this regard, the configuration depicted in FIG. 2A must be considered a transitory state or configuration, since the impeller housing will expand essentially immediately once unconstrained by the sheath.

It is notable that when impeller housing 104 is compressed, as depicted in FIG. 2A, its outer diameter is less than that of fixed-diameter impeller 120. When, however, impeller housing 104 is expanded, as depicted in FIG. 2B, its inner diameter is greater than that of fixed-diameter impeller 120.

Figure 2C:
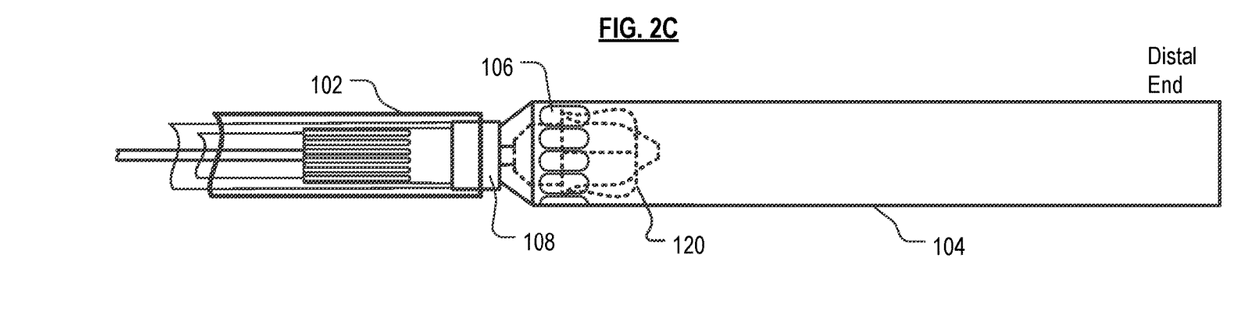
FIG. 2C depicts a second configuration of the distal portion of the catheter blood pump of FIG. 1A.

The configuration depicted in FIG. 2B is not the operational (i.e., pumping) configuration; rather, that configuration is depicted in FIG. 2C. As depicted in FIG. 2C, the configuration of catheter blood pump 100 is altered such that fixed-diameter impeller 120 is now disposed within impeller housing 104. Specifically, the impeller is disposed at the proximal end of impeller housing 104. When catheter blood pump is operating, the rapidly rotating fixed-diameter impeller 120 draws in blood through the distal end of impeller housing and expels it through openings 106.

Figure 4A:
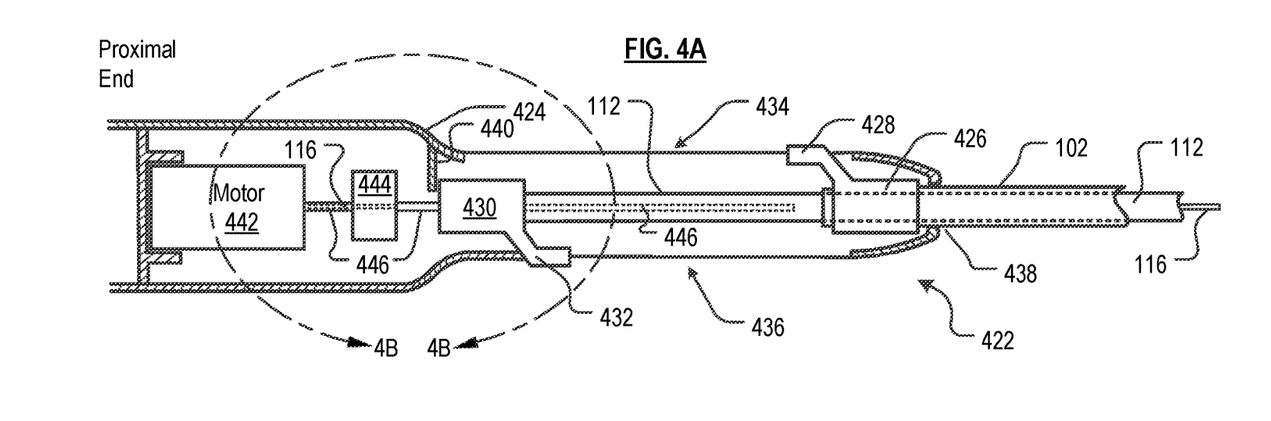
FIG. 4A depicts a handle containing an actuator for conducting some of the operations of the method of FIG. 3.

FIG. 4A depicts handle 422, which is an embodiment of motor assembly 670 (FIG. 6). Handle 422 includes housing 424, having proximal opening 438, and slots 434 and 436. Housing 424 contains motor 442, manifold 444, distal slideable member 426 and proximal slideable member 430.

Sheath 102, which enters housing 424 through distal opening 438, physically couples to distal slideable member 426. Outer tube 112 and inner tube 114 (not depicted) pass through distal slideable member 426 and physically couple to proximal slideable member 430. Slideable members 426 and 430 include respective finger pads 428 and 432 that are accessible to a clinician via respective slots 434 and 436. Sliding slideable member 426 proximally (toward slideable member 430) causes sheath 102 to retract by a like distance. Sliding slideable member 430 distally (toward slideable member 426) causes impeller housing 104 to advance a like distance (recalling that via the coupling of the inner and outer tubes 112 and 114 to bearing 108, and impeller housing 104 to bearing 108, the impeller housing moves with the inner and outer tubes). As discussed further in conjunction with FIGS. 5A through 5E, the slideable members are manipulated to reconfigure catheter blood pump 100. Stop 440 limits travel in the proximal direction of slideable member 430.

Drive cable 116 is operatively coupled to motor 442, and passes through manifold 444 and slideable members 430 and 426, exiting through distal opening 438. Hypo tube 446 surrounds drive cable 116 near motor 442, extends from the manifold, and passes through proximal slideable member 430. In some embodiments, hypo tube 446 terminates near to the proximal end of slideable member 426, since it serves as a rail or guide along which slideable member 430 slides. Slideable member 426 slides along the outer tube 112.

Figure 4B:
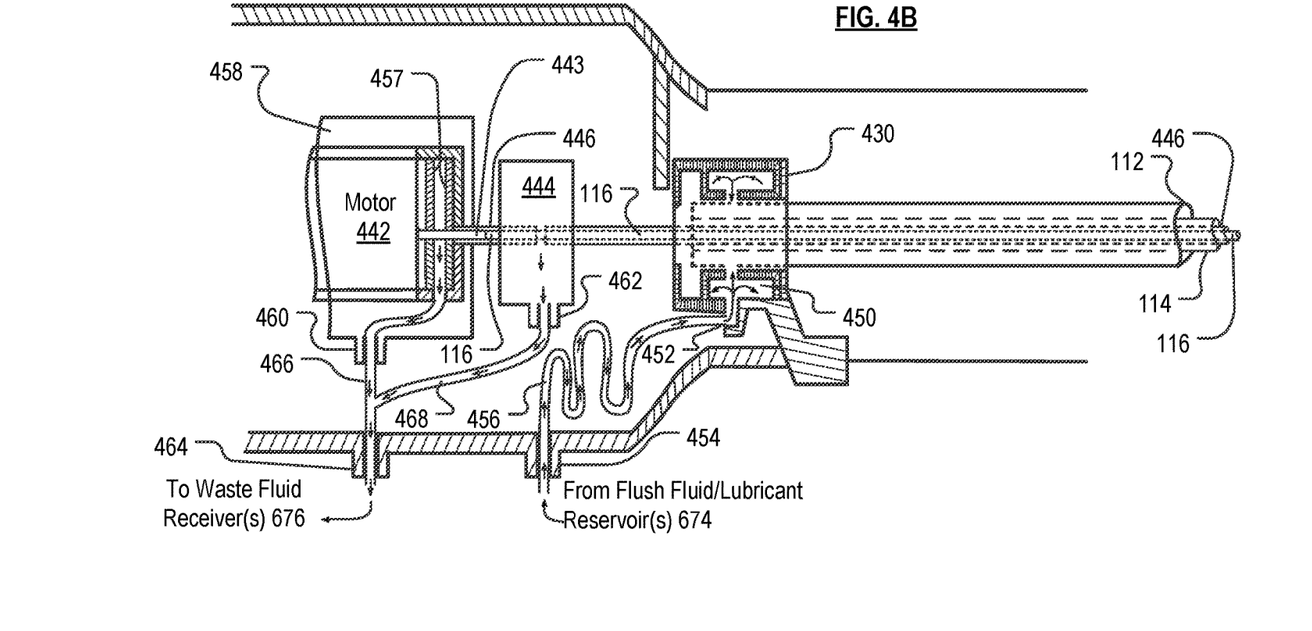
FIG. 4B depicts further detail of a portion of the handle of FIG. 4A.

FIG. 4B depicts an enlargement of the encircled region in FIG. 4A. This figure depicts an embodiment of the internal structure of slideable member 430, and depicts the flow of flush fluid/lubricant into and out of catheter blood pump 100.

Fluid inlet port 454 in housing 424 is fluidically coupled to inlet 452 of slideable member 430 via conduit 456. Fluid inlet port 454 receives flush fluid/lubricant from reservoir(s) 654. Conduit 456 delivers such fluids to inlet 452, which feeds annular cavity 450. Annular cavity 450 surrounds outer tube 112 in slideable member 430. Openings in outer tube 112 enable fluid to flow, under pressure, into the gap between the outer tube and inner tube 114. As previously discussed, the fluid travels between these two tubes until reaching bearing 108, at which point the fluid passes through holes 111 in the bearing (see, e.g., FIG. 1D), thereby wetting drive cable 116.

Waste fluids (i.e., flush fluid/lubricant contaminated by debris, etc.) flow towards the proximal end of drive cable 116 under pressure, and are removed at fluid outlet port 464 of housing 424, which is fluidically coupled to waste fluid receiver(s) 676. More particularly, waste fluids are withdrawn from drive cable 116 at manifold 444. Seals 457 prevent fluids that flow from drive cable 116 to motor shaft 443 from entering motor 442. Port 462 of manifold 444 and port 460 of motor housing 458 are fluidically coupled to fluid outlet port 464 by respective conduits 468 and 466. The waste fluid thus flows through these conduits and the fluid outlet port to the waste fluid receiver(s).

Conduit 456 is of sufficient length to accommodate forward movement of slideable member 430, as described in conjunction with FIGS. 4A, and in more detail with respect to FIGS. 5A-5E.

Figure 3:
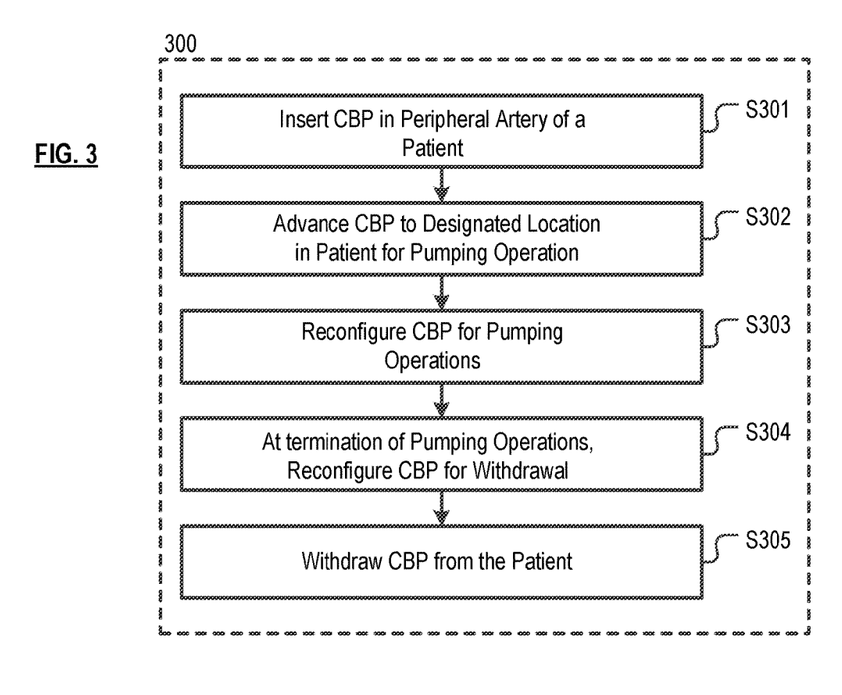
FIG. 3 depicts a method for using a catheter blood pump in accordance with the illustrative embodiment of the invention.

FIG. 3 depicts method 300 for operating catheter blood pump 100. In accordance with operation S301, the catheter blood pump is inserted into a peripheral artery of a patient, typically the femoral artery. This is routinely performed in the cath-lab, via a procedure commonly known as the Seldinger technique. Once inserted, the distal end of the catheter blood pump is advanced through the vasculature to the desired site as per operation S302, which is typically the across the aortic valve. For operations S301 and S302, catheter blood pump 100 is in the configuration depicted in FIG. 5A. In this configuration, impeller housing 104, but not fixed-diameter impeller 120, is situated within sheath 102. In the illustrative embodiment, this configuration is achieved by having slideable member 430, which controls movement of impeller housing 104, in a retracted or proximal position, and slideable member 426, which controls movement of sheath 102, in an advanced or distal position.

Figure 5A:
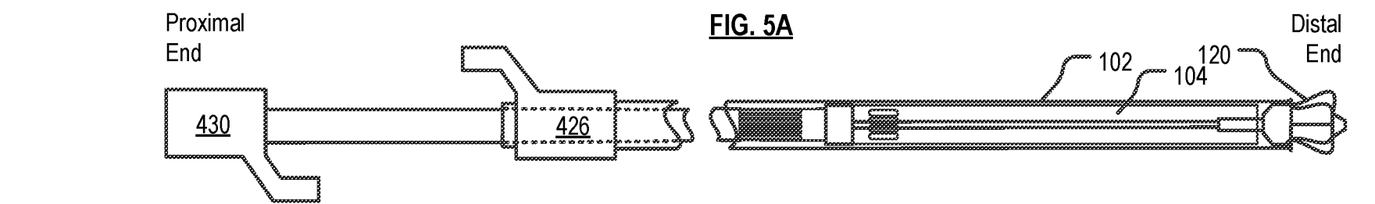
FIG. 5A depicts the proximal and distal ends of catheter blood pump of FIG. 1A, as configured for introduction to the vascular system.
Figure 5B:
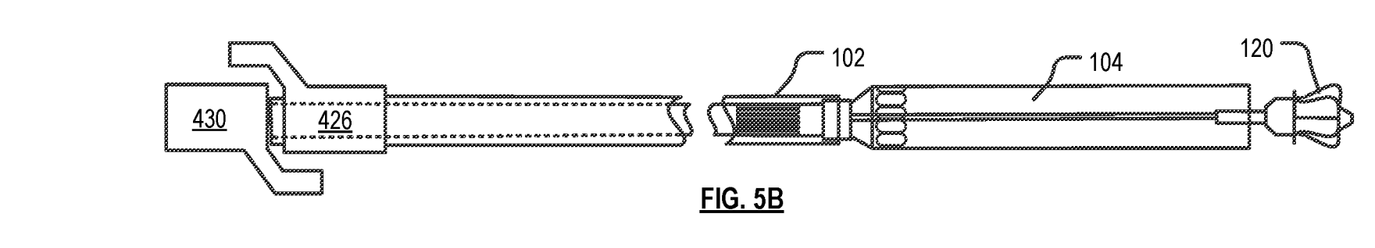
FIG. 5B depicts the proximal and distal ends of catheter blood pump of FIG. 1A in an intermediate configuration, as it is being reconfigured for pumping operations.
Figure 5C:
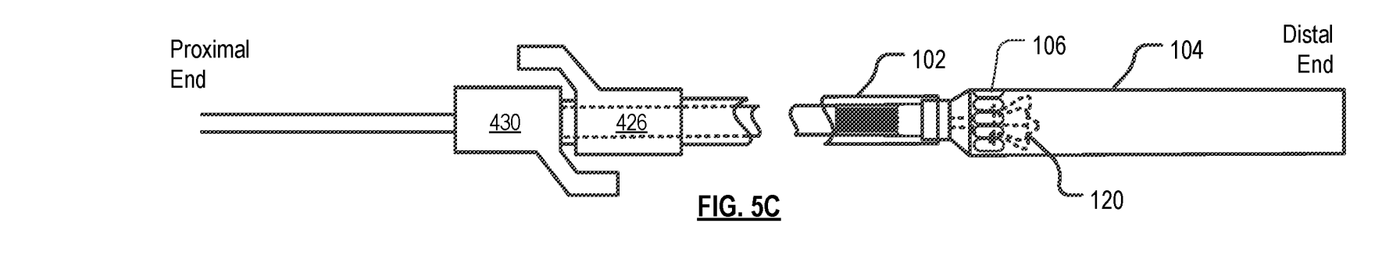
FIG. 5C depicts the proximal and distal ends of catheter blood pump of FIG. 1A, as configured for pumping operations.
Figure 5D:
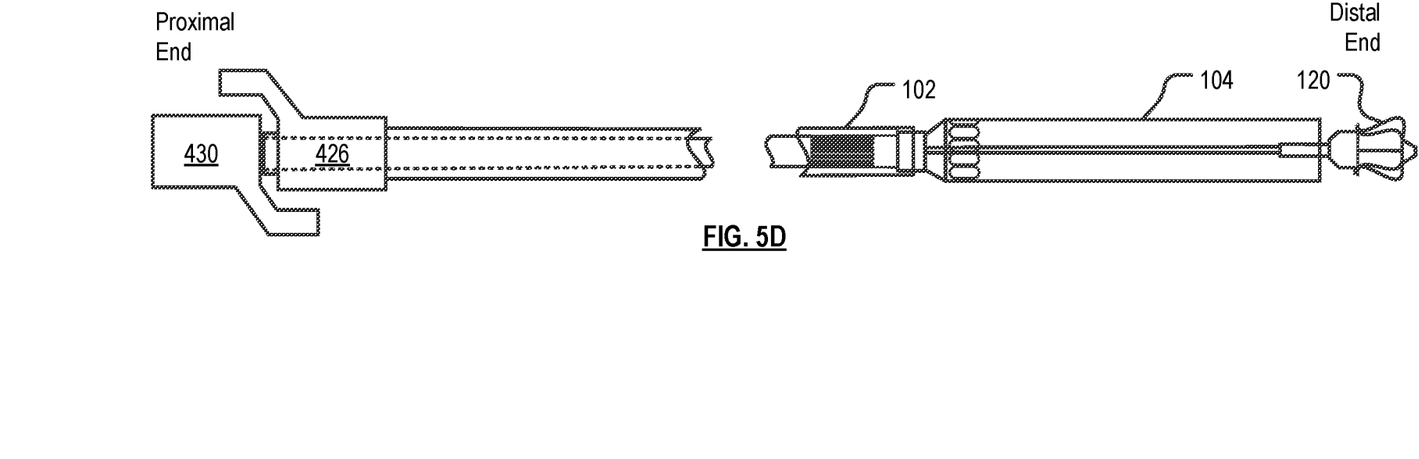
FIG. 5D depicts the proximal and distal ends of catheter blood pump of FIG. 1A in an intermediate configuration, as it is being reconfigured for withdrawal from the vascular system.

In operation S303, catheter blood pump 100 is reconfigured for pumping operations. In the illustrative embodiment, this is a two-step process. In a first step, as depicted in FIG. 5B, slideable member 426 is retracted (moved proximally) against slideable member 430. This causes sheath 102 to retract, freeing impeller housing 104 and thereby allowing it to expand. At the end of this first step, fixed-diameter impeller 120 is still the distal-most portion of catheter blood pump 100, and is exposed to the anatomy. In a second step, which is depicted in FIG. 5C, slideable member 430 is advanced (moved distally), advancing slideable member 426 with it. This causes both sheath 102 and impeller housing 104 to advance, such that fixed-diameter impeller 120 is captured within the impeller housing, near the proximal end thereof. Note that in this operation, the impeller housing and the sheath do not move relative to one another; they move distally in concert. Protected from the anatomy by expanded impeller housing 104, pumping operations may begin.

During pumping operations (if the impeller housing is sited across the aortic valve), blood enters the distal end of impeller housing 104 from the left ventricle of the heart. The blood crosses the aortic valve through the impeller housing and is discharged through openings 106 into the ascending aorta.

Figure 5E:
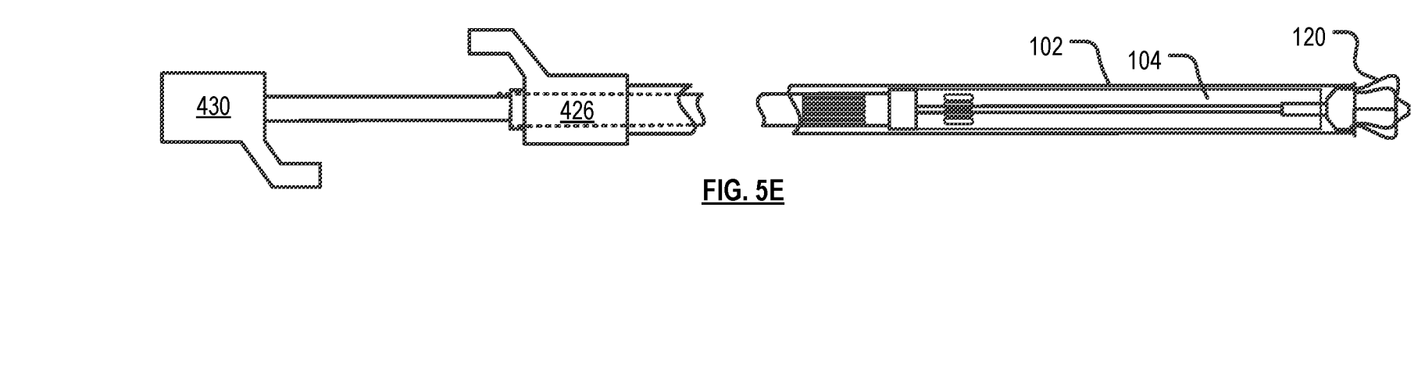
FIG. 5E depicts the proximal and distal ends of catheter blood pump of FIG. 1A, as configured for withdrawal from the vascular system.

At the termination of pumping operations, which will typically last for several hours to one or more weeks, catheter blood pump 100 is once again reconfigured, this time for removal from the vasculature. As before, reconfiguration involves two steps. In a first step depicted in FIG. 5D, slideable member 426 is retracted (moved proximally), retracting slideable member 430 with it. This retracts both sheath 102 and impeller housing 104 (no relative motion therebetween), with the result that fixed-diameter impeller 120 no longer remains in the impeller housing. This places catheter blood pump 100 in the same configuration as in FIG. 5B. And in a second step, which is depicted in FIG. 5E, slideable member 426 is advanced (moved distally), which advances sheath 102 over impeller housing 104, causing the impeller housing to contract in diameter as it does so. Catheter blood pump is now configured for withdrawal, and has the same configuration as depicted in FIG. 5A for insertion.

It will be appreciated by those skilled in the art that there a variety of ways to create relative movement between the sheath, expandable housing, and drive cable to achieve the two basic configurations (i.e., (i) insertion/withdrawal and (ii) operation) for the catheter blood pump, as discussed below.

In the illustrative embodiment, sheath 102 and impeller housing 104 are independently moved while drive cable 116/impeller 120 remain in a fixed axial location. In a first alternative embodiment, sheath 102 and the drive cable/impeller are independently moved while impeller housing 104 remains in a fixed axial location. In such an embodiment, sheath 102 is retracted (i.e., moved proximally), thereby freeing impeller housing 104 to expand. Drive cable 116 is retracted (i.e., moved proximally), moving fixed-diameter impeller 120 into the expanded impeller housing, readying the catheter blood pump for pumping operations. After pumping operations are complete, drive cable 116 is advanced (moved distally) so that fixed-diameter impeller 120 exits the confines of impeller housing 104. Sheath 102 is then advance (moved distally), which forces impeller housing 104 to contract in diameter, the impeller housing moving wholly within the sheath.

In a second alternative embodiment, only impeller housing 104 is movable; sheath 102 and drive cable/impeller remain in fixed axial locations. In this embodiment, impeller housing 104 is advanced (i.e., moved proximally), expanding as it moves beyond sheath 102, and continuing to advance until fixed-diameter impeller 102 is in its desired operational location within the impeller housing and near its proximal end (i.e., proximate to openings 106).

In embodiments in which a drive cable is not used (i.e., internal motor), the motor and fixed-diameter impeller 120 are moved, rather than the drive cable and fixed-diameter impeller 120.

To the extent other such alternative methods are used to reconfigure catheter blood pumps in accordance with the present teachings, modifications to handle 422 (FIG. 4A) may be required. Such modifications are within the capabilities of those skilled in the art.

Summarizing, the catheter blood pump, as depicted and previously described, comprises: (i) a fixed-diameter impeller; (ii) a sheath; and (iii) an expandable impeller housing. The catheter blood pump may further comprise at least one of the following features, in any (non-conflicting) combination:

a motor that delivers torque to the fixed-diameter impeller;
a drive cable that is coupled to the fixed-diameter impeller for transmitting torque thereto;
the diameter of the fixed-diameter impeller is substantially equal to or greater than the outer diameter of the largest-diameter tube of the catheter blood pump that is inserted into the vascular system;
the diameter of the fixed-diameter impeller is larger than outer diameter of the sheath;
the sheath has the largest external diameter of any of the plurality of fixed-diameter tubes of the blood pump that are inserted into the vasculature, wherein fixed-diameter impeller is too large to reside within the sheath;
the fixed-diameter impeller is disposed at the distal end of the blood pump and is the distal-most feature thereof as it is advanced through the vasculature;
the impeller housing has two states, one in which it is compacted/compressed such that its diameter is reduced, and in which state it resides within the sheath, and a second in which it is external to the sheath, wherein the impeller housing expands to size suitable for positioning the fixed-diameter impeller therein;
the impeller housing includes a plurality of holes disposed proximate to the proximal end thereof, through which blood flows out of the impeller housing during operation of the catheter blood pump;
the impeller housing includes an opening at a distal end thereof, wherein in operation, blood is drawn through the opening;
the impeller housing is physically coupled to the distal side of a bearing;
inner and outer tubes are physically coupled to the proximal side of the bearing, wherein flush fluid and/or lubricant flow(s) toward the bearing through a gap between the inner and outer tubes;
a plurality holes disposed radially through the bearing to enable flush fluid and/or lubricant that flow(s) through the gap between the inner and outer tubes to pass through the bearing onto the drive cable.
an actuator that is physically adapted to place the catheter blood pump in at least two physical configurations, one for insertion/removal/advancement through the vasculature and a second for pumping;
an actuator that is physically adapted to cause relative movement in an axial direction among the sheath, the impeller housing, and the fixed-diameter impeller;
an actuator that is physically adapted to independently move, in an axial direction, the sheath and the impeller housing, but not move the fixed-diameter impeller;
an actuator that includes a first slideable member and a second slideable member, each independently movable in the axial direction, wherein the first slideable member physically couples to a proximal end of the sheath, and the second slideable member is operatively coupled to the impeller housing;
an actuator that includes a first slideable member and a second slideable member, each independently movable in the axial direction, wherein the first slideable member is operatively coupled to the sheath, and the second slideable member is operatively coupled to the impeller housing, wherein three positions of the slideable members are required to place the catheter blood pump in two states, one for movement through the vascular system and the second for pumping operations;
an actuator that includes at least a first slideable member, wherein the first slideable member is fluidically coupled to a source of flush fluid and/or lubricant;
an actuator that includes a distal-most slideable member and a proximal-most slideable member, each independently movable in the axial direction, wherein the actuator includes a hypo tube that passes through the proximal-most slideable member along the axial direction to guide movement thereof;
an actuator that includes a first slideable member and a second slideable member, each independently movable in the axial direction, wherein the first slideable member physically couples to a proximal end of the sheath, and the second slideable member is operatively coupled to the impeller housing, and wherein the actuator further includes a motor;

an actuator that is physically adapted to independently move, in an axial direction, the sheath and the fixed-diameter impeller, but not move the impeller housing, to place the pump in the at least two physical configurations;
an actuator that is physically adapted to move the impeller sheath in an axial direction, but not move the sheath and not move the fixed-diameter impeller, to place the pump in the at least two physical configurations;
an actuator that includes a single slideable member that is movable in the axial direction, wherein the first slideable member is operatively coupled to the impeller housing;
proximal of a bearing that stabilizes the fixed-diameter impeller during pumping operations, the catheter blood pump consists of the following tubes, in order of smallest diameter to largest diameter: an inner tube, an outer tube, and a sheath;
an actuator that is physically adapted to independently move, in an axial direction, the sheath and the impeller housing, but not move the fixed-diameter impeller, consists of the following tubes, in order of smallest diameter to largest diameter: a hypo tube, an inner tube, an outer tube, and a sheath;

It is to be understood that the disclosure describes a few embodiments and that many variations of the invention can easily be devised by those skilled in the art after reading this disclosure and that the scope of the present invention is to be determined by the following claims.

The following claims are presented for examination:

1. A catheter blood pump, the catheter blood pump including a plurality of fixed-diameter tubes that are inserted into a patient's vascular system, the catheter blood pump comprising:
    a fixed-diameter impeller, wherein the fixed-diameter impeller is operatively coupled to a motor, the fixed-diameter impeller having a first diameter;
    an impeller housing that is expandable from a collapsed state to an expanded state;
    a sheath, wherein the sheath has the largest external diameter of the plurality of fixed-diameter tubes, and wherein the first diameter of the fixed-diameter impeller is too large for the fixed-diameter impeller to reside within the sheath; and
    an actuator, wherein the actuator is physically adapted to place the catheter blood pump in at least two physical configurations, including:
    a) a first configuration in which the impeller housing within the sheath is in the collapsed state, and in which the fixed-diameter impeller is distal relative to the impeller housing and is a distal-most feature of the catheter blood pump;
    b) a second configuration in which the impeller housing is external to and substantially distal of the sheath and is in the expanded state, and wherein the fixed-diameter impeller is disposed within the impeller housing at a proximal end thereof.

2. The catheter blood pump of claim 1 further comprising a drive cable, wherein the drive cable operatively couples the motor to the fixed-diameter impeller, and wherein the drive cable passes through the sheath.

3. The catheter blood pump of claim 1 wherein the actuator is physically adapted to cause relative movement in an axial direction among the sheath, the impeller housing, and the fixed-diameter impeller.

4. The catheter blood pump of claim 1 wherein the actuator is physically adapted to independently move, in an axial direction, the sheath and the impeller housing, but not move the fixed-diameter impeller, to place the pump in the at least two physical configurations.

5. The catheter blood pump of claim 4 wherein the actuator comprises a first slideable member and a second slideable member, each independently movable in the axial direction, wherein the first slideable member physically couples to a proximal end of the sheath, and the second slideable member is operatively coupled to the impeller housing.

6. The catheter blood pump of claim 1 wherein the actuator is physically adapted to independently move, in an axial direction, the sheath and the fixed-diameter impeller, but not move the impeller housing, to place the pump in the at least two physical configurations.

7. The catheter blood pump of claim 1 wherein the actuator is physically adapted to move the impeller sheath in an axial direction, but not move the sheath and not move the fixed-diameter impeller, to place the pump in the at least two physical configurations.

8. The catheter blood pump of claim 1 wherein the impeller housing includes a plurality of openings through the surface thereof and wherein all of the openings are disposed proximate to the proximal end of the impeller housing.

9. A catheter blood pump, the catheter blood pump including a plurality of fixed-diameter tubes that are inserted into a patient's vascular system, the catheter blood pump comprising:
    a fixed-diameter impeller having a first diameter;
    a drive cable operatively coupled to a motor at a proximal end thereof, and operatively coupled to the fixed-diameter impeller at a distal end thereof;
    a sheath, wherein the sheath has a second diameter, which is the outer diameter thereof and the largest diameter of any of the plurality of fixed-diameter tubes, and wherein the first diameter is at least as large as the second diameter; and
    an impeller housing having:
    (a) a collapsed state wherein the impeller housing resides with the sheath, and further wherein the fixed-diameter impeller is disposed at a distal end of the sheath and a major portion of the fixed-diameter impeller is external thereto, and
    (b) an expanded state wherein the impeller housing is external to the sheath and has an inner diameter greater than the first diameter.

10. The catheter blood pump of claim 9 and further wherein, in an operating state of the catheter blood pump, the impeller housing is in the expanded state and the fixed-diameter impeller is disposed at a proximal end of the impeller housing and internal thereto.

11. The catheter blood pump of claim 9 further comprising an actuator, wherein the actuator is physically configured to move at least one of the sheath or the impeller housing to reconfigure the impeller housing to the collapsed state from the expanded state, and to reconfigure the impeller housing to the expanded state from the collapsed state.

12. The catheter blood pump of claim 11 wherein the actuator is physically adapted to independently move, in an axial direction, the sheath and the fixed-diameter impeller, but not move the impeller housing.

13. The catheter blood pump of claim 11 wherein the actuator is physically adapted to move the impeller housing in an axial direction, but not move the sheath and not move the fixed-diameter impeller.

14. A catheter blood pump, the catheter blood pump including a plurality of fixed-diameter tubes that are inserted into a patient's vascular system, the catheter blood pump comprising:

a fixed-diameter impeller having a first diameter;

a drive cable operatively coupled to a motor at a proximal end thereof, and operatively coupled to the fixed-diameter impeller at a distal end thereof;

a sheath, wherein the sheath has a second diameter, which is the outer diameter thereof and the largest diameter of any of the plurality of fixed-diameter tubes, and wherein the first diameter is at least as large as the second diameter;

an impeller housing having:
(a) a collapsed state wherein the impeller housing resides with the sheath, and
(b) an expanded state wherein the impeller housing is external to the sheath and has an inner diameter greater than the first diameter; and an actuator that is physically adapted to independently move, in an axial direction, the sheath and the impeller housing, but not move the fixed-diameter impeller.

15. The catheter blood pump of claim 14 wherein the actuator comprises a first slideable member and a second slideable member, each independently movable in the axial direction, wherein the first slideable member physically couples to a proximal end of the sheath, and the second slideable member is operatively coupled to the impeller housing.

16. The catheter blood pump of claim 14 wherein the actuator comprises:

a housing;

a first slideable member disposed partially within the housing, wherein a portion of the first slideable member is accessible at an external surface of the housing, and wherein the first slideable member is operative to cause translational movement of the sheath; and a second slideable member disposed partially within the housing, wherein a portion of the second slideable member is accessible at the external surface of the housing, and wherein the second slideable member is operative to cause translational movement of the impeller housing.

17. The catheter blood pump of claim 16 wherein the first slideable member is accessible at a first portion of the external surface of the housing and the second slideable member is accessible at a second portion of the external surface of the housing.

18. The catheter blood pump of claim 17 wherein the first portion and the second portion are located at opposite sides of the external surface of the housing.

19. A catheter blood pump, the catheter blood pump including a plurality of fixed-diameter tubes that are inserted into a patient's vascular system, the catheter blood pump comprising:

a fixed-diameter impeller having a first diameter;

a drive cable operatively coupled to a motor at a proximal end thereof, and operatively coupled to the fixed-diameter impeller at a distal end thereof;

a sheath, wherein the sheath has a second diameter, which is the outer diameter thereof and the largest diameter of any of the plurality of fixed-diameter tubes, and wherein the first diameter is at least as large as the second diameter; and an impeller housing having:
(a) a collapsed state wherein the impeller housing resides with the sheath,
(b) an expanded state wherein the impeller housing is external to the sheath and has an inner diameter greater than the first diameter, and the fixed-diameter impeller is disposed at a proximal end of the impeller housing and internal thereto; and
(c) a plurality of openings through the surface thereof and wherein all of the openings are disposed proximate to the proximal end of the impeller housing.

20. A catheter blood pump including a plurality of fixed-diameter tubes that are inserted into a patient's vascular system, the catheter blood pump comprising:

a fixed-diameter impeller having a first diameter;

a sheath having a second outer diameter, wherein the first diameter is at least as large as the second outer diameter;

an impeller housing having:
(a) a first state, wherein the impeller housing resides within the sheath and further wherein the fixed-diameter impeller is at a distal end of the catheter blood pump, and
(b) a second state, wherein the impeller housing is external to the sheath and wherein the fixed-diameter impeller is within the impeller housing and at a proximal end thereof.

21. A catheter blood pump including a plurality of fixed-diameter tubes that are inserted into a patient's vascular system, the catheter blood pump comprising:

a fixed-diameter impeller having a first diameter;

a sheath, wherein the sheath is the largest of the fixed diameter tubes, and wherein, as a consequence of the first diameter, the fixed-diameter impeller cannot fit within the sheath;

an impeller housing, wherein the impeller housing is expandable and contractible in diameter; and an actuator, wherein the actuator is operable to cause to the impeller housing to expand in diameter to place the catheter blood pump in a first state, and to cause the impeller housing to contract in diameter to place the catheter blood pump in a second state, wherein:
a) in the first state, the catheter blood pump is configured for pumping operations, wherein (i) the impeller housing is in an expanded-diameter state, and (ii) the fixed-diameter impeller is disposed in the impeller housing; and
b) in the second state, the catheter blood pump is configured for movement through the vascular system, wherein (i) the impeller housing is in a contracted-diameter state and is disposed within the sheath, and (ii) the fixed-diameter impeller is not contained in any tube or other structure of the catheter blood pump.

* * * * *